United States Patent [19]

Berkman et al.

[11] Patent Number: 4,750,489
[45] Date of Patent: Jun. 14, 1988

[54] RADIAL KERATOTOMY KNIFE AND SYSTEM USING SAME

[75] Inventors: John W. Berkman, Costa Mesa; Michael H. Curtis, El Toro; David A. Dewey, Huntington Beach, all of Calif.

[73] Assignee: CooperVision, Inc., Menlo Park, Calif.

[21] Appl. No.: 770,528

[22] Filed: Aug. 29, 1985

[51] Int. Cl.$^4$ .................. A61B 17/32; A61F 17/32
[52] U.S. Cl. .................... 128/314; 128/305; 351/205
[58] Field of Search .............. 128/305, 660, 314; 30/320, 338, 294; 33/172 E, 169 B; 351/205; 250/231 P

[56] References Cited

U.S. PATENT DOCUMENTS

| | | | |
|---|---|---|---|
| 4,324,044 | 4/1982 | Shahinian, Jr. | 30/294 |
| 4,340,059 | 7/1982 | Marinoff | 128/305 |
| 4,406,285 | 9/1983 | Vissasenor et al. | 128/305 |
| 4,473,076 | 9/1984 | Williams et al. | 128/305 |
| 4,499,898 | 2/1985 | Knepshield et al. | 128/305 |
| 4,516,575 | 5/1985 | Gerhard et al. | 128/305 |
| 4,546,773 | 10/1985 | Kremer et al. | 128/660 |

OTHER PUBLICATIONS

Schaevitz Technical Bulletin 10002D, "LVDT and RVDT Linear and Angular Displacement Transducers", 5/85.
Silicon Detector Corp., "Position Sensors" (Quad Detection Circuitry).
KOI Associates, Model KO 100000-21/Model KO 100000-21 (Diamond Knife).

Primary Examiner—V. Millin
Assistant Examiner—H. Macey
Attorney, Agent, or Firm—Vorys, Sater, Seymour and Pease

[57] ABSTRACT

A radial keratotomy knife which includes an accurate linear position transducer for digitally displaying the extension of a surgical blade beyond a footplate on the knife. A system is also disclosed for zeroing the blade position relative to the footplate. The system includes a zeroing sleeve having a reflective membrane to reflect light to a detector. The knife is inserted into the sleeve so that the footplate is in contact with the membrane within the system contained within a console. When the blade is advanced to contact the reflective membrane from within the sleeve, the reflected light pattern is altered to establish accurately a zero position of the knife blade relative to the footplate. The knife is then withdrawn from the sleeve and the blade advanced by a micrometer so that the transducer produces a signal relative to the reference level indicating the extension of the blade.

44 Claims, 6 Drawing Sheets

RADIAL KERATOTOMY KNIFE AND SYSTEM USING SAME

BACKGROUND OF THE INVENTION

This invention relates to an accurate, repeatable radial keratotomy knife. More particularly, this invention relates to a system for accurately zeroing and determining the blade extension of a radial keratotomy knife which includes an accurate linear position transducer therein. Still more particularly, this invention relates to a method and apparatus which includes a radial keratotomy knife having a linear position transducer mounted therein and connected to a circuit for accurately displaying the blade extension after zeroing. Still more particularly, this invention relates to a method and apparatus for zeroing the blade extension of the radial keratotomy knife by using a sleeve with a membrane to reflect light to a detector so that contact of the blade of the keratotomy knife with the membrane indicates a reference or datum position.

A procedure is known for the surgical correction of myopia and/or astigmatism by radial keratotomy. In this procedure, a series of radial, non-penetrating incisions are made on the periphery of the cornea, in order to alter its shape, and consequently aid in correcting the condition.

For use in such procedures, a radial keratotomy knife is known having a size and shape suitable for being held in the hand of the surgeon. Such knives include a body having a nose piece housing a footplate for receiving a blade assembly. The knife includes a structrue for advancing or retracting the blade assembly relative to the footplate to control to a high degree of accuracy the extension of the blade beyond the footplate. Such devices require visual comparison under a microscope with a predetermined physical gauge. Examples of such a knife and a gauge for determining blade extension are shown in U.S. Pat. No. 4,499,898 to Knepshield.

Such a technique is not completely advantageous because of certain inaccuracies in the technique. A major source of inaccuracy resides in the judgmental step of zeroing the blade relative to the footplate in the initial stages in order to determine the number of rotations of the knob on the handpiece to advance the blade.

Accordingly, it is an overall object of this invention to provide an improved radial keratotomy knife which has an accurate and repeatable mechanism for determining the blade extension.

It is another object of this invention to provide a keratotomy knife having a linear position transducer capable of producing an output voltage with sufficient sensitivity to display the blade extension after zeroing on the order of 1–2 microns.

It is an additional object of this invention to provide an apparatus for use with a radial keratotomy knife of the type described wherein the zeroing of the blade relative to the footplate is accurately determined to act as a reference extension for subsequent advances of the blade, while continuing to achieve the accuracy of the order indicated.

It is still another object of this invention to provide a console unit having an electronic digital readout when secured to a knife of the type described which also will receive the knife in combination with a zeroing device to establish the measuring datum when the tip of the blade is precisely in alignment with the adjacent prongs of the footplate.

It is still another object of this invention to provide a zeroing device for a knife of the type described which comprises a sterile, disposable sleeve having a membrane attached thereto for reflecting light in a system.

It is another general object of this invention to provide a console unit for receiving the knife and sleeve combination and reflecting light from the membrane in order to zero the blade extension when the footplate is in contact with the mirror-forming membrane.

These and other objects of this invention will become apparent from the following detailed written description of the invention, taken in conjunction with the accompanying drawings.

BRIEF SUMMARY OF THE INVENTION

Directed to achieving the foregoing objects and overcoming the shortcomings of currently available radial keratotomy knives, the invention relates to such a knife having means for sensing the position of a surgical blade relative to a reference position to provide an electrical signal indicative thereof. In a preferred embodiment, a linear position transducer, preferably a linear variable differential transformer (LVDT) is incorporated within the body of the knife intermediate a rotatable member and the blade so that the position of the core of the transformer causes an electrical output proportional to the displacement of the core. Circuit means are provided for energizing the transformer and for sensing the net output of the transducer to provide a digital display of the blade extension.

Means are also provided for zeroing the blade extension of the knife relative to a footplate. The zeroing means takes the form of a sterile disosable sleeve having a flexible, reflective membrane on one end. The sleeve is structurally adapted to receive the knife with its blade retracted therein, so that the footplate on the knife non-invasively contacts the reflective membrane. A system is provided for receiving the combination of the handpiece and sleeve in a holder on the face of a console which is accurately located with respect to a beam of light and an optical detector. A beam of light, preferably a laser, focuses on the detector after reflection from the mirror formed by the membrane in contact with the footplate. Upon advancing the blade until it contacts the membrane, a change in the pattern of reflection from the membrane is detected to constitute a zero level when the blade tip is at a plane defined by the prongs of the footplate. Such a technique determines a reference or datum level for the blade tip relative to the footplate which is electronically translated to a zero digital readout. After zeroing, the digital readout determined by advancing or retracting the core of the transducer within the knife, after removal from the sleeve, accurately indicates the position of the knife tip, while eliminating reliance on the accuracy of the adjusting screw.

DETAILED DESCRIPTION OF THE PREFERRED EMBODIMENT

Figure 1:
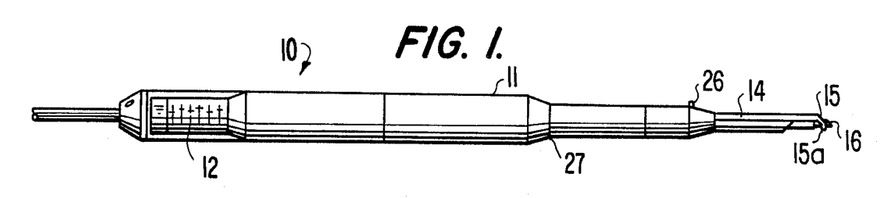
FIG. 1 is a pictorial side view of a radial keratotomy knife according to the invention.
Figure 2:
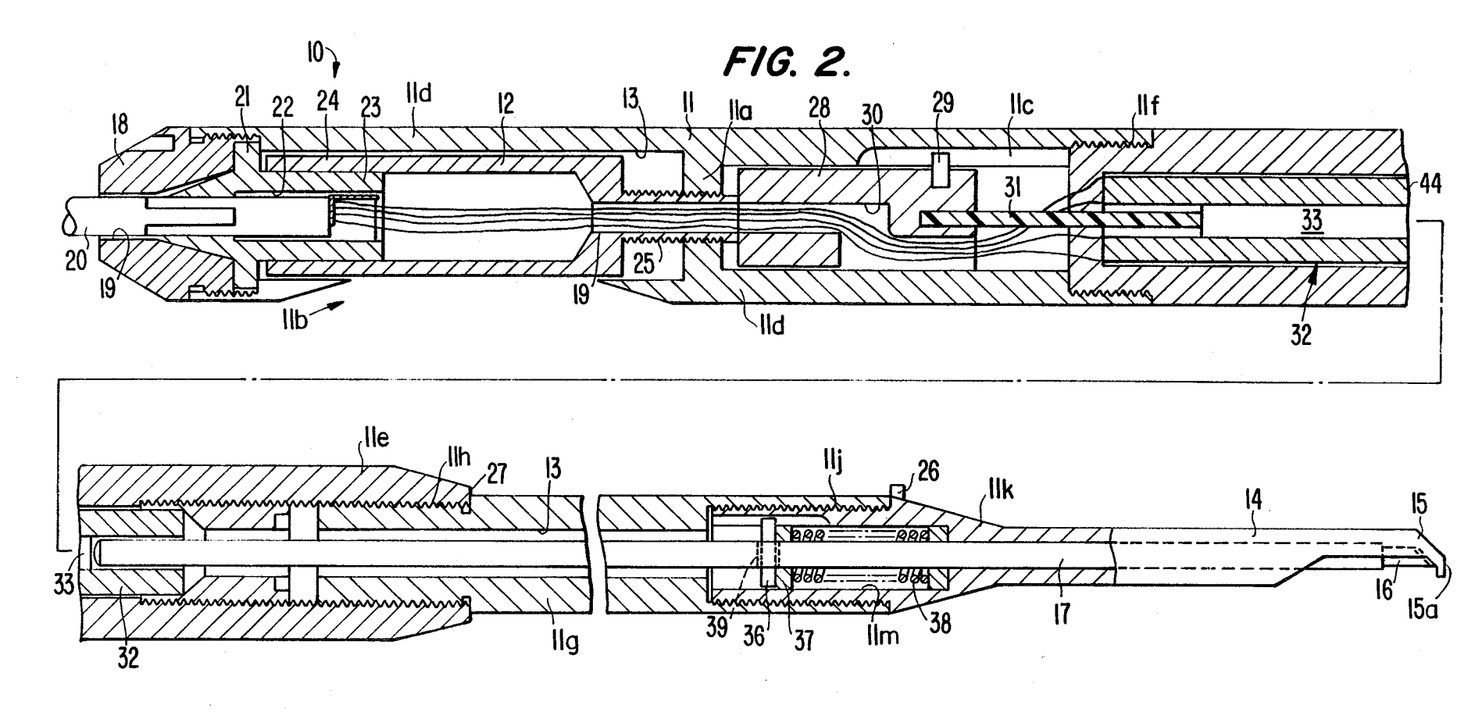
FIG. 2 is a detailed side cross sectional view of the radial keratotomy knife shown in FIG. 1 further depicting the linear variable differential transformer (LVDT) and its movable core.

An accurate, repeatable radial keratotomy knife according to the invention is shown in FIGS. 1 and 2 and is designated by the reference numeral 10. The knife 10 includes an elongated body 11 defining a bore therethrough and having a rotatable positioning member 12 near one end thereof. At the opposite, or forward end of the knife, a footplate 14 is secured as a part of a blade assembly which is threadably secured to the body 11. The footplate 14 includes a pair of opposed prongs 15 defining a space therebetween through which the tip 16 of a blade assembly 17 protrudes. The body 11 is constructed to define a handpiece to be held in the hand of a surgeon in performing a keratotomy procedure wherein the length of the extension of the tip 16 of the blade beyond the plane of the surface 15a of the footplate is critical.

Rotation of the rotating member 12 causes the blade assembly 17 to move axially to extend or withdraw the blade tip 16 relative to the surface 15a. The rotating member 12 is fixedly rotatably secured in the bore 13 of the body 11 by advancing threads 25 mating with threads formed on an internal threaded shoulder 11a within the body 11. A cap member 18 defines a bore 19 therein through which an electrical cable 20 is passed to be connected to an appropriate electronic digital readout located distant from the knife 10. The cable 20 is sufficiently light and flexible to avoid or minimize interference with the user.

A fixed connecting member 21 also defining a bore 22 for receiving the cable 20 therein includes a cylindrical support portion 23 for stably but rotatably supporting a cyindrical end portion 24 of the rotatable member 12. The member 12 is manually caused to rotate about its threads 25 because of its freely rotating connection at the portion 24 to the member 21, and is accessed by the fingers of the user through an opening 11b in the body of the knife. A nonrotating but axially-slidable member 28 is secured within the body 11 by an anti-rotation pin 29 axially movable in an axial channel 11c in the body 11. The member 28 defines a passage 30 through which a plurality of leads pass to be connected to the cable at their one end and to a transducer designated generally by the reference numeral 32. The nonrotating member 28 is connected to a core-contacting member 31, preferably a non-magnetic material, adjacent a core 33 of the transducer 32. One end of an axially-extending blade assembly 17 is secured in a bore of the transducer adjacent the core 33 opposite the member 31 and is pierced by an anti-rotation pin 36, which passes through a transverse hole 39 in the blade assembly 17. The components of the body 11 are arranged compactly within the bore 13 to avoid axial and rotational play by the blade assembly 17. The knife 10 further includes an indexing pin 26 for orienting the knife when inserted in the sleeve of FIG. 6.

The pin 36 abuts against a plate 37 axially biased by a cylindrical spring 38 interposed between the plate 37 and the end of a spring activity 11m in a member 11k. Thus, a clockwise rotation of the member 12 moves the member 28 axially to the right, correspondingly moving the member 31, the core 33, and blade assembly 17 to the right against the force of the spring 38, advancing the tip of the blade 16 relative to the footplate 15. Conversely, counterclockwise rotation of the member 12 causes, through the same relatively-fixed, axially slideable parts, the blade to retract.

Preferably, the body of the knife comprises the cap member 18 and a first body portion 11d, housing the rotatable member 12 and the nonrotating member 28 and defining the internal shoulder 11a and the axial slot 11c. The body portion 11d has a relatively larger diameter. A second body portion 11e housing the commercially available transducer 32 is threadedly secured at 11f to the first body portion 11d and has about the same diameter as the first body portion. A third body portion 11g is threadedly secured as at 11h to the forward end of the body portion 11e and houses the blade assembly 17. The third body portion is preferably of a smaller diameter than the second body portion and is threaded as at 11j to receive the forward body portion 11k housing the distal portion of blade assembly 17.

Figure 3:
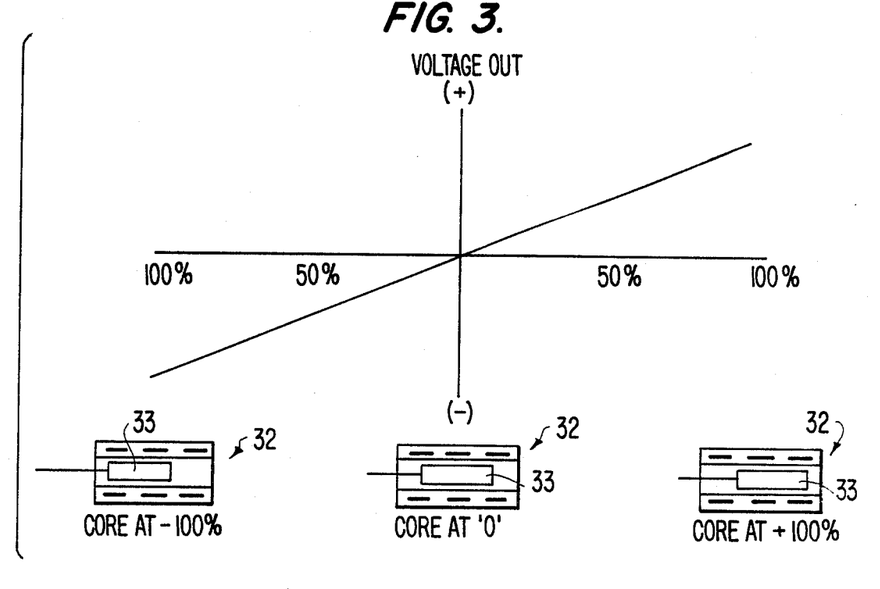
FIG. 3 is a graphical depiction of the output of the LVDT superimposed on pictorials of the core, thus showing transducer output as a function of core position.
Figure 4:
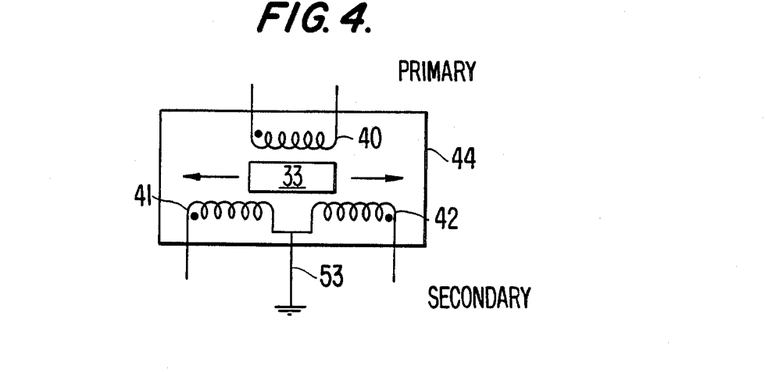
FIG. 4 is a generalized electrical schematic of the LVDT used in the preferred embodiment.

The transducer 32 in the embodiment shown in preferably a linear variable differential transformer (LVDT), a device which is commercially available. As is known, an LVDT is an electromechanical device that produces an elecrtrical output accurately proportional to the displacement of a separate movable core 33. As is shown in FIG. 3, the voltage output from the transducer 32 is linear over a range of travel of the core from its remote positions within the body of the knife. As seen in FIG. 4, an LVDT consists of a primary coil 40 and a pair of secondary coils 41 and 42 disposed relative to the core 33 and symmetrically spaced on a cylindrical form 44 fixedly secured in the body 11. The free-moving, rod-shaped magnetic core 33 within the coil assembly provides a path for the magnetic flux linking the coils 40, 41, and 42.

When the primary coil 40 is energized by an external source through the cable 20 and the associated leads 30, voltages are induced in the secondary coils 41 and 42. The secondary coils are connected in a series opposing relationship so that the voltages of the respective secondaries are of opposite polarity. Thus, the net output of the transducer 32 is the difference between the two voltages of the secondaries 41 and 42, which is zero, as shown in FIG. 3, when the core 33 is at a center or null position. As the core 33 is moved from its null position by rotating the knob 12 and advancing the core or withdrawing the core, the induced voltage in the coil toward which the core is moved increases while the induced voltage in the opposite coil decreases. This repositioning of the core 33 produces a differential voltage output that varies linearly, and accurately, as shown in FIG. 3, with changes in core position. The phase of the output voltage changes abruptly by 180° as the core 33 is moved from one side of the null to the other. Accordingly, the knife 10 as described in connection with FIGS. 1-4, provides an accurate repeatable output signal which can be digitally interpreted to indicate the core position and hence the position of the blade tip. For the embodiment shown with a linear transducer with the type described, the resolution and accuracy of the knife is on the order of plus or minus 1.5 microns.

Figures 5, 6:
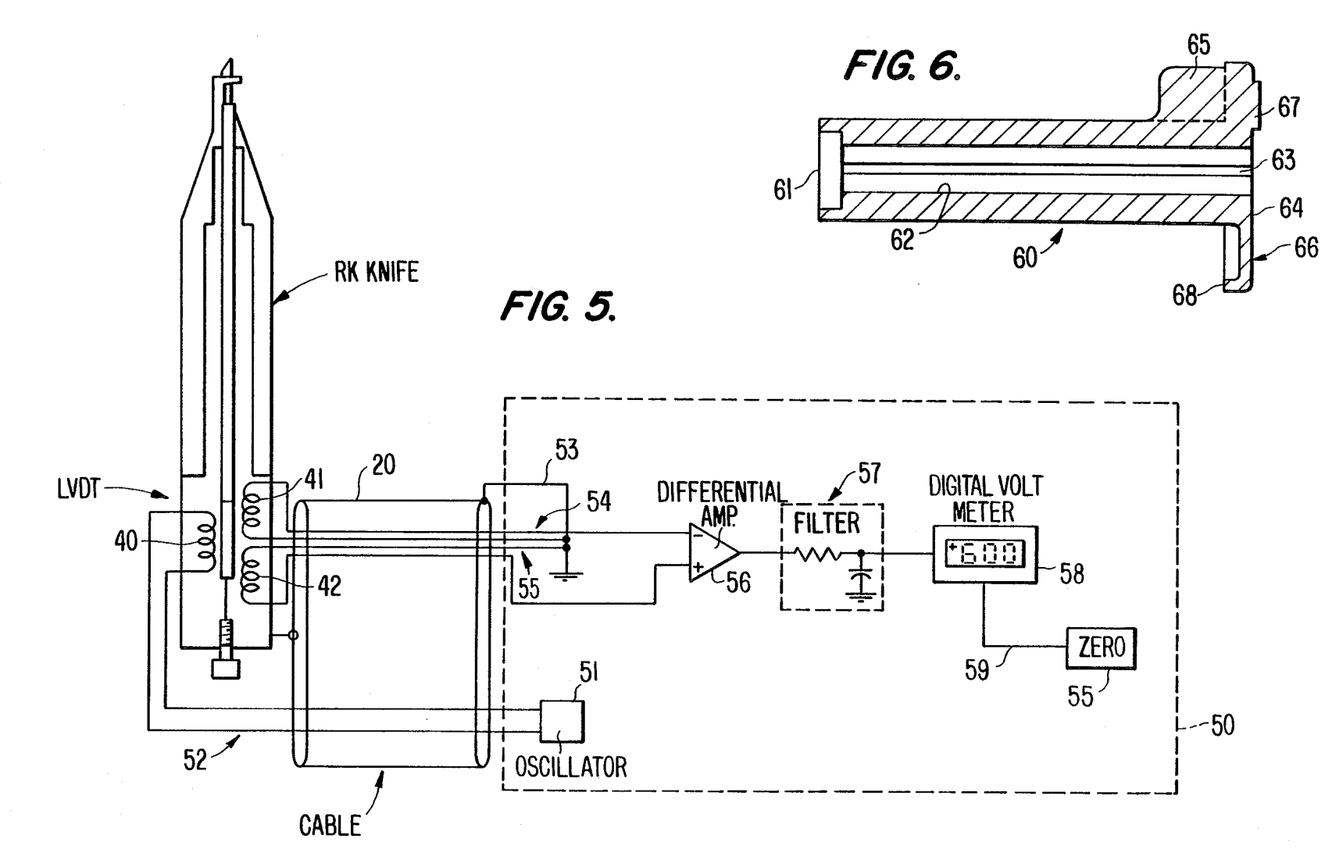
FIG. 5 is a block diagram of a circuit connected to the transducer on the knife for digitally displaying the position of the knife blade relative to the footplate.
FIG. 6 is a side cross sectional view of a zeroing device for the knife in the form of a sleeve having a reflective membrane, for receiving the knife according to the invention.

FIG. 5 shows a block diagram of the complete measuring circuit wherein like reference numerals are shown as used in FIGS. 1-4. The electronic circuit components are preferably housed in a console 50 having an AC oscillator 51 connected to a pair of leads 52 directly connected to the primary coil 40 the LVDT while the secondary coils 41, 42 have their common lead grounded to the cable 20 by a connection 53. The secondary leads 54 and 55 respectively provide the minus and plus inputs to a differential amplifier 56 having its output connected to a filter 57 in turn connected to a digital volt meter (DVM) 58. The DVM 58 connected to a zeroing circuit by a lead 59 for setting the digital display to zero upon command, using techniques well known in the electronics art.

It remains, therefore, to electronically establish with a corresponding high degree of accuracy a zero or datum position of the tip of the blade relative to the footplate. Accordingly, as shown in FIG. 6, a zeroing device in the form of a hollow, axially-extending sleeve consists of a sterile, disposable sleeve 60 which has a reflective plastic membrane 61 connected at one end thereof. The sleeve 60 defines a knife receiving bore 62 for securing therein by a hand connection the knife 10 as described in connection with FIGS. 1 and 2 in a way so that the footplate 14 abuts the membrane 61 but does not extend therethrough. The bore 62 defines a keyway 63 extending therealong for mating with a corresponding protrusion or pin 26 on the knife 10.

The pin 26 fixes the orientation of the knife within the sleeve 60 to assure a satisfactory focus of the light beam at a predetermined point or area on the membrane 61. This relationship is thus desirable because, in usual circumstances, the surface 15a of the footplate 15 is normally located slightly off the center axis of the knife 10. By predetermining the relative disposition of the knife within the sleeve, and the sleeve within the console, a predetermined location on the membrane can be targeted to focus the light beam during the zeroing process.

The sleeve 60 further defines an axially extending fin 65 on the forward side of the flange 66 on the sleeve 60. The fin 65 mates with a corresponding slot on the console 50 to assure the orientation described above and also provides a light-interrupting surface to trigger an opto-switch to signal that the sleeve is located within the console 50. An upwardly-raised portion 67 is located on the side of the flange 66 opposite to the fin 65 to aid the operator visually and tactually in locating the sleeve in the console 50.

The flange 66 defines a reference surface 68 which cooperates with the console 50 in accurately positioning the sleeve 60 within the console relative to the light source. The length of the sleeve is such relative to the knife that the footplate positively contacts the membrane 61 without protruding excessively in order to assure the reflective conditions needed during the zeroing procedure.

In use, the distal end of the handpiece or knife 10 is placed in the sleeve 60 so that the shoulder 27 of the knife 10 rests against an end surface 64 of the flange 66 of the sleeve 60 and the footplate 15 has the membrane stretched lightly across its surface 15a. The combination of the sleeve 60 and the knife 10 is inserted in a mating opening in the console 50 (see FIG. 8) having a beam detection circuit shown schematically in FIG. 7.

Figure 7:
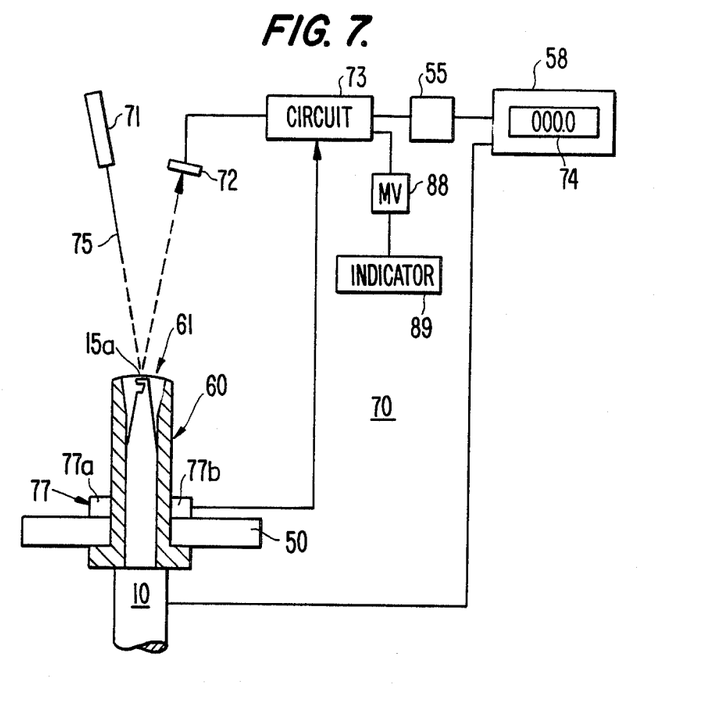
FIG. 7 is a schematic view of a beam detector circuit for determining a zero or datum level for the knife blade position relative to the footplate.

The beam detection circuit of FIG. 7 is shown generally by the reference numeral 70 and comprises a source of light 71, which is preferably a laser source, and a four quadrant opitcal detector 72 having its output connected to an electronic detecting circuit 73 and to a digital voltmeter 58. The output may also be used to activate the zeroing circuit 55 of FIG. 5, or the circuits 55 and 73 may be combined to operate a single DVM. The light beam, designated generally by the reference numeral 75, from the light source 71 is focused on the detector 72 after reflection from a mirror formed by the footplate 15 in contact with the reflective plastic membrane 61 at the end surface of the sleeve 60. The pattern of light striking the detector 72 will be uneven, but distinctive and constant, so that the electronic circuit 73 is able to detect very small changes in this pattern. In practice, the rotating member 12 of the knife 10 is rotated until the tip 16 of the knife blade assembly 17 touches the membrane 61, thus changing its shape. Almost instantaneously, the pattern of light reflected from the membrane 61 to the detector 72 changes drastically and is detected by the electronic circuit 73. Preferably, the output of the display 58 is electronically caused to be instantly reset to zero as discussed in connection with FIG. 5 so that, from this time on, the digital readout 74 will accurately locate the position of the knife tip 16 relative to the footplate surface 15a without depending upon the accuracy of an observer.

The position of the light or laser beam 75, as described, is detected by a photodiode quadrant detector 72. A quad detector 72 and a quad detection circuit 73 are commercially available. As is thus known, quadrant detectors sense position deviations of a light spot about the optical axis of a system. Such measurements may be made over a range equal to the diameter of the light spot to detect minute fluctuations near the null point. The position information is derived from two current signals for each axis which are proportional to the precise location of the laser spot 75 on the surface of the detector 72. The two current signals are first converted to voltages by transimpedence amplifiers after which both the difference and sum of those two voltage signals are obtained. The ratio of the difference divided by the sum of those signals provides an accurate measurement of position which is independent of the intensity of the laser beam 75. Two such computations provide the x and y position of the laser beam for utilization in the electronic circuitry 73.

Figure 11:
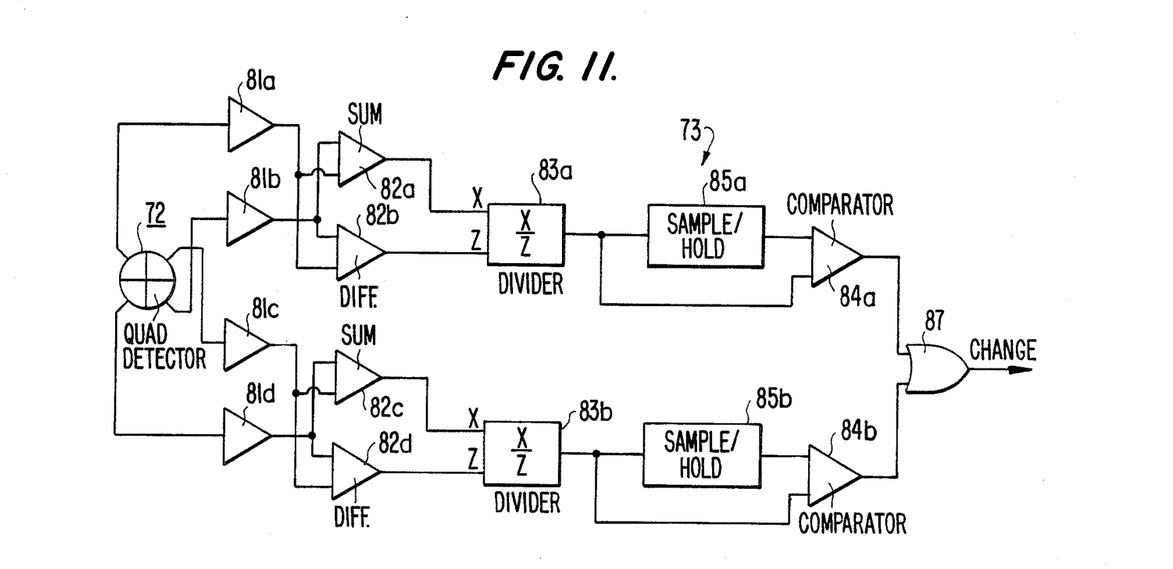
FIG. 11 is a more detailed schematic, partially in block form, of the beam detector circuit used in a preferred embodiment of the invention.

FIG. 11 shows a schematic diagram in block form for an available beam detection circuit wherein the quadrant detector 72 provides an output signal for each of four quadrants to a respective one of a plurality of transimpedance preamplifiers. The preamplifiers 81a and 81b define the x channel, while the preamplifiers 81c and 81d define the y channel. The output from the amplifier 81a provides an input to each of a pair of sum and difference amplifiers 82a, 82b which provide the inputs to a divider 83a which divides the sum of the signals from the amplifiers 81a and 81b (from the summing amplifier 82a) by the difference between those same two signals from the amplifiers 82b. The output from the divider 83a provides an input to a comparator 84a and a sample and hold circuit 85a. Similarly, the output from the summing amplifier 82c and the output from the difference amplifier 82d are connected to a divider circuit 83b which provides an input to a comparator 84b and a sample and hold circuit 85b. The outputs from the comparators 84a, 84b are connected to a gate 87 to produce an output signal representing a change in position of the signal.

In operation, referring to FIGS. 7 and 11, upon insertion of the sterile sleeve 60 into the console 50, an optical switch 77 on an inner surface of the face of the console 50 is interrupted by the fin 65 on the sleeve 60. The switch 77 has an emitter 77a and a receiver 77b. The optical switch provides an output signal which inhibits the circuit for a predetermined period of time, such as one second. During the inhibited period, a sample is taken of the position of the beam 75 on the quad detector 72. This sample is held indefinitely in the sample and hold circuits 85a and 85b and that signal is used to set the window center of a window comparator circuit. After the inhibit period has expired, any significant change in beam position will trigger the window comparator circuit by operation of the circuit of FIG. 11. The window compartor fires a one shot MV 88 which drives an electronic buzzer 89 for an audio output. At the same time, the sample and hold circuits 85a and 85b are triggered to sample the analog output of the LVDT circuit and this sample is held indefinitely to be used to offset the op amp input to a DVM circuit which provides an auto zero capability. Thus, any change in the LVDT will show up on the DVM 58 relative to the auto zero point.

Figures 8, 10:
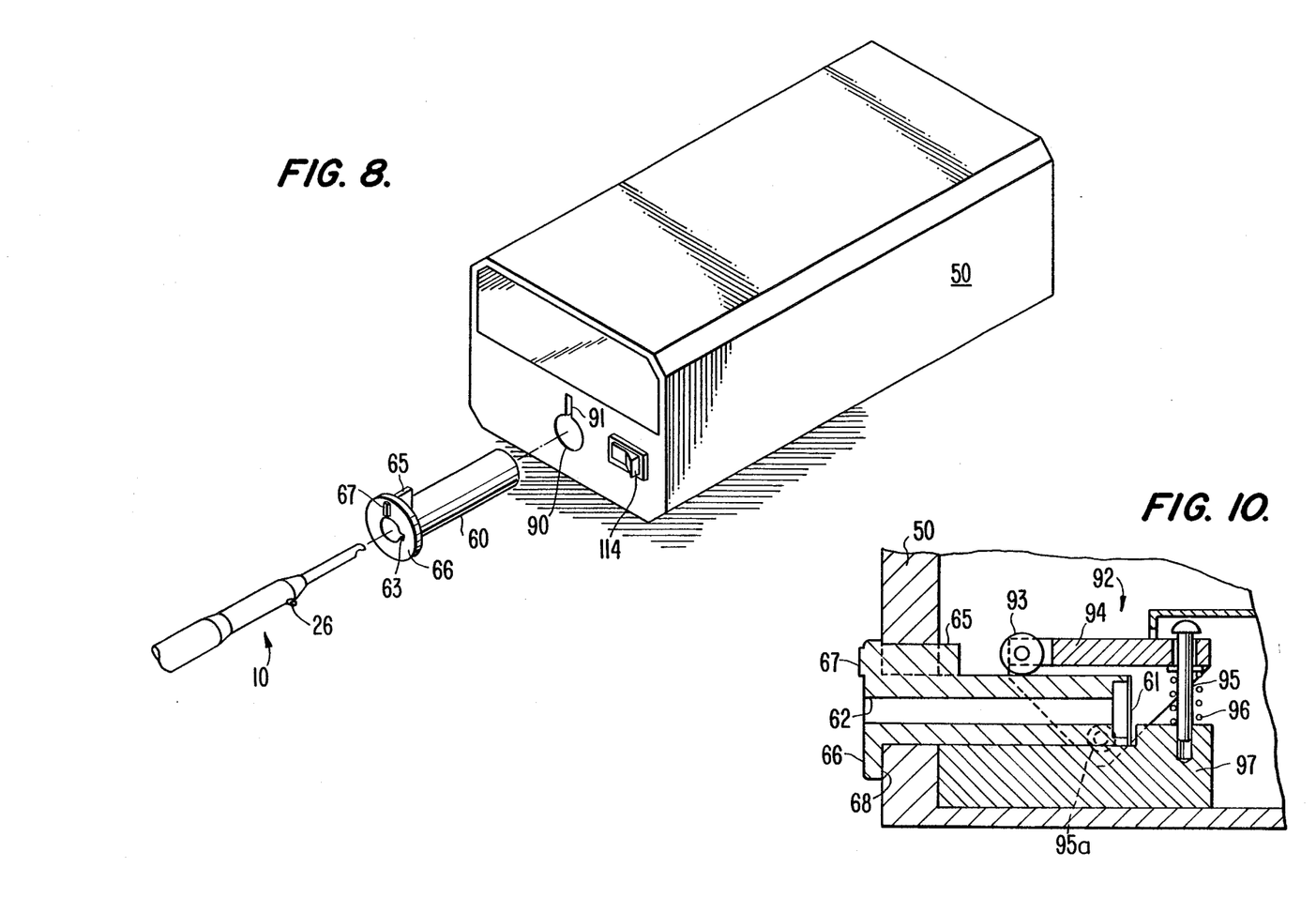
FIG. 8 is an exploded perspective view of the knife, its mating and zeroing sleeve, and a console containing otpical and electrical circuits for receiving the combination of the sleeve and the knife for establishing a zero or datum level for the blade extension relative to the footplate.
FIG. 10 is a cross sectional view taken along line 10—10 of FIG. 9 showing the mechanical structure for securing the zeroing device relative to the face of the console, and an optoswitch for sensing that the sleeve is in place.
Figure 9:
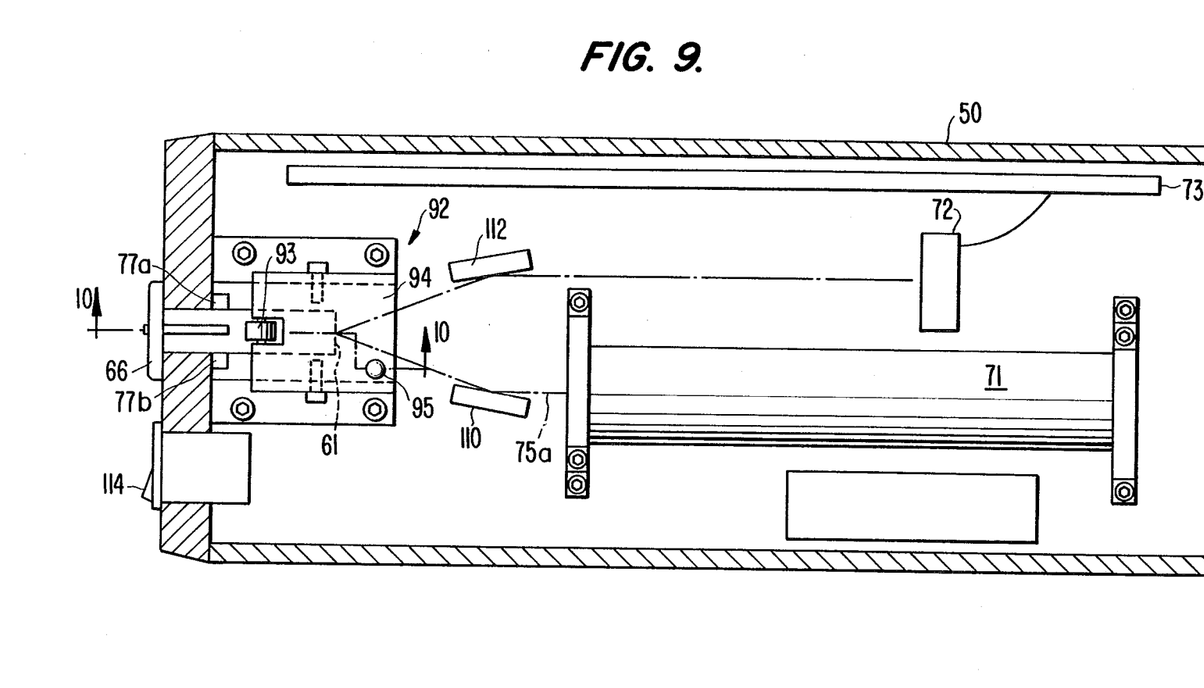
FIG. 9 is a generalized top view of the console with its top removed showing a preferred optical circuit and a mechanism for mechanically receiving the zeroing sleeve.

Referring now to FIGS. 8-10, the physical implementation of the knife according to FIGS. 1-4, the sleeve of FIG. 6, and the zeroing circuits of FIGS. 7 and 11 will be described. As shown in FIG. 8, the knife 10 is oriented relative to the sleeve 60 so that the indexing pin 26 can slide, upon insertion, along the axial slot 63 in the sleeve 60. The console 50 defines a sleeve receiving opening 90 in its front face having an indexing opening 91 for receiving therethrough the fin 65 on the flange 60. After the knife 10 has been inserted in the sleeve, an operator may tactually and visually know of the orientation of the fin 65 by touching or viewing the member 67 on the face of the flange 66 of the sleeve. The combination of the sleeve 60 and the knife 10 is thus inserted into the opening 90.

During insertion, as shown in FIG. 10, the sleeve 60 is pressed downwardly by a sleeve retaining mechanism 92 shown generally at comprising a forward roller 93 carried at the end of a member 94 which is mounted pivotally about a pin 96. A spring 96 is interposed between a base member 97 secured in the interior of the console 50 and the lower surface of the member 94. Pin 95 acts as a spring guide and counterclockwise rotation stop. The mechanism 92 exerts a downward force on the sleeve 60 during insertion while permitting easy axial movement.

The fin 65 has a length greater than the thickness of the forward wall of the console to interrupt an optical circuit having the optical switch 77 discussed in connection with FIG. 7. Preferably, the emitter 77a and the receptor 77b are located on the inner wall of the front surface of the console 50 in such a way that upon insertion of the sleeve 60, the fin 65 interrupts the optical circuit therebetween to trigger the events described in connection with FIGS. 7 and 11. The reference surface 68 on the sleeve 60 contacts the front face of the console to determine the optimum location for performing the sensitive optical measurement during the zeroing process described above.

In the embodiment shown in FIG. 9, the principles of operation of the optical circuit are substantially the same as those described in connection with FIG. 7. However, in that case, the light source 71 is preferably a laser emitting a light beam 75a which is reflected to change its direction by a first mirror 110 to impinge on the reflective membrane 61 on the sleeve 60. The reflected light from the membrane 61 is redirected by a mirror 112 to the photodetector 72 and its associated circuitry 73.

In use, the console 50 is connected to a suitable source of electrical power and a power switch 114 on the console 50 turned to its (on) position. In order to prepare the knife for performing the zero adjustment, the micrometer adjustment knob, or rotating member 12 is turned counterclockwise so that the blade 17 and its tip 16 are retracted to a protected position just below the exterior surface 15a of the footplate 15. Thereafter, the knife and blade assembly are sterilized according to conventional procedures and the sterilized knife 10 is placed in the sterile field. The cable 10 is then secured to the electronic console 50. A sterile sleeve 60 is removed from a sterile pack and the knife 10 inserted into the sleeve until the sleeve abuts against the shoulder 27 of the knife. The assembly of the sleeve 60 and the knife 10 is then inserted into the calibration port 90 on the console 50 and the micrometer knob 12 rotated until the display 74 displays 0.000 and an audible tone is heard from the indicator 89. This action occurs for the reasons described in connection with FIGS. 7-11. If desired, the circuit can be arranged to provide a second audible tone when the blade is projected beyond a predetermined distance, such as ten microns.

After attaining a zero setting, as described, the knife 10 is removed from the sleeve 60 while the sleeve 60 remains in the console 50 until the conclusion of the surgical procedure. Thereafter, the desired blade length is adjusted by rotating the micrometer knob 12 clockwise until the LED displays, with a plus or minus five microns accuracy, a blade protrusion in the range of 10 to 800 microns.

Preferably, the reflective plastic membrane 61 used with the invention is a 0.0005 inch thick plastic film, e.g., a biaxially oriented film of polyethylene terephthalate marketed as "Mylar", which is particularly suited to use with the invention because of its reflectivity and its strength in resisting tearing while flexing sufficiently to practice the invention. The quadrant detector and the detector circuitry are available, for example, from Silicon Detector Corporation, Newbury Park, Calif.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

We claim:

1. A knife system comprising:
   a body;
   a member in said body;
   a footplate secured to said body, said footplate defining a reference location;
   a blade having a tip, said blade being axially movable and movably secured to said body so that said tip can be extended or withdrawn relative to said reference location;
   means for causing said blade to be so extended or withdrawn;
   transducer means for sensing the position of said member whose position is related to the position of said tip relative to said reference location and for providing an output signal indicative thereof;
   circuit means connected to said transducer means for providing said electrical signal to electronic means for displaying a value representative of the extension of said tip relative to said reference location; and
   a member including means structurally adapted to receive said blade therein and reflecting means for providing a reflective surface indicative of said reference location, said member further including sensing means for sensing contact between said reference location and said reflecting means to provide a basis for determining when said tip is at said reference location.

2. The knife system as set forth in claim 1 wherein said transducer means comprises a linear position transducer.

3. The knife system as set forth in claim 2 wherein said linear position transducer is a linear variable differential transformer.

4. The knife system as set forth in claim 1 wherein said reflective surface is a reflective plastic film and said member is a tubular sleeve.

5. The knife system as set forth in claim 4 wherein said blade includes a first indexing member and said sleeve includes a second indexing location, said first indexing member and said second indexing location being structurally adapted to permit said blade to be received in said sleeve in a predetermined orientation.

6. The knife system as set forth in claim 5 wherein said sleeve includes a forward extending fin for mating with a corresponding opening in a console which houses a light source, a light detector, and a detection circuit, said fin and said opening together predetermining the orientation of said sleeve when inserted in a face of the console.

7. The knife system as set forth in claim 5 including a console housing a light source, a light detector, and a detection circuit, said console having a console opening and a console face, said sleeve including a forward extending fin for mating with said console opening, said fin and said opening together predetermining the orientation of said sleeve when inserted in said console face.

8. The knife system as set forth in claim 7 including said light source being accurately positioned relative to said reflective surface, said console including a light receiving member, and a signal circuit means connected to said detector for providing an output signal indicative of contact of said reference location with said reflective surface.

9. The knife system as set forth in claim 8 including said signal circuit means being in said console.

10. The knife system as set forth in claim 8 including said signal circuit means including a determining means for determining when said knife blade contacts said reflective surface to establish a zero level indicating that said tip is at said reference location.

11. The knife system as set forth in claim 10 including said determining means determining said contact through optical and electrical means.

12. The knife system as set forth in claim 1 including said electronic means being external to said body.

13. The knife system as set forth in claim 1 including said electronic means being external to said blade.

14. The knife system as set forth in claim 1 including a circuit means with which said sensing means cooperates.

15. The knife system as set forth in claim 1 including said member being disposable.

16. The knife system as set forth in claim 1 including said member being a structural member.

17. A sleeve for use in optical and electrical circuits for determining a reference position of a tip of a knife having a knife blade in a surgical instrument relative to a reference location defined by a footplate of the knife, said sleeve comprising:
    a body defining a hollow bore therein for receiving the knife therein; and
    a reflective, flexible member located at one end of said body at a position in contact with the footplate of the knife when located in said bore to establish a first optical condition capable of being sensed by optical and electrical circuits, said flexible member establishing a second optical condition capable of being sensed by the optical and electrical circuits when the tip of the knife is extended beyond the footplate and contacts said flexible member.

18. The sleeve as set forth in claim 17 further including a slot along said bore for receiving therein a mating pin on the knife, said slot and the pin together establishing the orientation of the knife within the body.

19. The sleeve as set forth in claim 18 wherein the length of said bore is substantially identical to a predetermined length of the knife on the forward end thereof so that the footplate lightly touches said reflective, flexible member from within said body.

20. The sleeve as set forth in claim 19 wherein said flexible member is a reflective plastic film.

21. The sleeve as set forth in claim 20 wherein said plastic film is biaxially oriented polyethylene terephthalate.

22. The sleeve as set forth in claim 21 further including a flange at the end of said body opposite said film, said flange defining a reference surface for determining accurately the length of insertion of the combination of the knife and said body within a measuring instrument.

23. The sleeve as set forth in claim 22 wherein said body includes an axially extending fin structurally adapted to be received in a slot, for determining the orientation of said body within said measuring instrument.

24. A surgical knife of the type comprising a body structurally adapted to be held in the hand of its user, a footplate, a blade having a tip, and micrometer means for manually advancing or withdrawing said tip relative to said footplate, the improvement comprising:
- sensing means for electromagnetically sensing the position of a member accurately representative of the position of said tip relative to said footplate, and providing an electrical output signal indicative thereof;
- determining means, including an optical sensor, for determining a reference position for said tip at said footplate and providing a reference signal indicative thereof;
- an electrical circuit means for receiving said electrical output signal and said reference signal and providing a signal representative thereof; and
- display means for receiving said position signal and for displaying a representation of the position of said tip relative to said footplate.

25. The surgical knife as set forth in claim 24 including said representation being a digital representation.

26. The surgical knife as set forth in claim 24 including a console housing said electrical circuit means, and said console and said electrical circuit means defining a measuring instrument.

27. The surgical knife as set forth in claim 26 wherein said sensing means is a transformer having a transformer primary and a transformer secondary, and said instrument includes a source of power for said transformer primary and an output taken from said transformer secondary.

28. The surgical knife as set forth in claim 27 including a cable connecting the body to said instrument.

29. The surgical knife as set forth in claim 28 including said transformer being a linear variable differential transformer.

30. The surgical knife as set forth in claim 24 wherein said circuit means includes a setting means for setting upon command said display means to zero.

31. The surgical knife as set forth in claim 30 wherein said display means is a digital display means.

32. An optical circuit for sensing a datum position for a tip of a blade of a surgical knife relative to a reference location defined by a footplate, comprising:
- a source of light,
- a flexible reflective member contactable with the footplate, said reflective member including establishing means for establishing a first optical condition when the tip is withdrawn from the footplate and a second optical condition when the tip is aligned with the footplate, said reflective member being adapted to receive and reflect light from said source of light,
- a detector means for sensing said first optical condition upon reflection of light from said reflective member when the tip is withdrawn from the footplate, and
- said reflective member comprising means for establishing said second optical condition upon reflection of light from said reflective member upon contact between the tip and said reflective member, said second optical condition establishing a datum or zero position.

33. The optical circuit as set forth in claim 32 wherein said source of light comprises a laser beam adapted to be reflected by said reflective member.

34. A method of determining a datum position for a tip of a blade of a surgical knife relative to a reference location defined by a footplate comprising the steps of:
- placing a reflective member in contact with said footplate while said tip is withdrawn from said reference location;
- reflecting a beam of light from said reflective member to a detector to determine a first optical condition;
- advancing said tip until it contacts said reflective member to establish a second optical condition upon reflection of said beam of light from the reflective member to said detector;
- detecting said first and second conditions to establish that said second optical condition indicates when said tip is at said datum position; and
- distinguishing said first and second optical conditions with circuit means to provide a signal indicative thereof.

35. The method as set forth in claim 34 wherein the step of placing further comprises the step of placing said surgical knife in a zeroing device which includes said reflective member at a position for contacting said footplate while said tip is withdrawn from said reference position.

36. The method as set forth in claim 35 wherein the step of placing further includes the step of orienting said knife within said zeroing means to assure a satisfactory focus for said beam of light on said reflective member.

37. The method as set forth in claim 34 wherein the step of reflecting is characterized in that said beam of light is a laser beam.

38. The method as set forth in claim 34 wherein the step of detecting is performed using an optical detector circuit.

39. The method as set forth in claim 34 wherein the step of distinguishing further includes the step of resetting a display to zero when said tip is in said datum position.

40. A surgical knife comprising:
- a body having a tip;
- a member in said body;
- a footplate secured to said body, and defining a reference location;
- a blade axially movable and movably secured to said body so that said tip can be extended or withdrawn relative to said reference location;
- means for manually causing said blade to be so extended or withdrawn;
- transducer means including a core member for sensing the position of said member in said body in contact with said core member, wherein the position of said core member is related to the position of said tip relative to said reference location and providing an output signal indicative thereof; and
- circuit means connected to said transducer means for providing said output signal to electronic means for displaying a value representative of the extension of said tip relative to said reference location.

41. The knife as set forth in claim 40 wherein said transducer means comprises a linear position transducer.

42. The knife as set forth in claim 41 wherein said linear position transducer is a linear variable differential transformer.

43. The surgical knife as set forth in claim 40 including said value being digitally displayed.

44. The surgical knife as set forth in claim 40 including said transducer means providing said signal to electronic means external to said body.

* * * * *